United States Patent
Dyba et al.

(10) Patent No.: US 9,772,485 B2
(45) Date of Patent: Sep. 26, 2017

(54) METHOD AND DEVICE FOR LIGHT-MICROSCOPIC IMAGING OF A SAMPLE STRUCTURE

(75) Inventors: Marcus Dyba, Heidelberg (DE); Volker Seyfried, Nussloch (DE)

(73) Assignee: Leica Microsystems CMS GmbH, Wetzlar (DE)

(*) Notice: Subject to any disclaimer, the term of this patent is extended or adjusted under 35 U.S.C. 154(b) by 513 days.

(21) Appl. No.: 13/806,047

(22) PCT Filed: Jun. 27, 2011

(86) PCT No.: PCT/EP2011/060688
§ 371 (c)(1),
(2), (4) Date: Dec. 20, 2012

(87) PCT Pub. No.: WO2012/000923
PCT Pub. Date: Jan. 5, 2012

(65) Prior Publication Data
US 2013/0222568 A1    Aug. 29, 2013

(30) Foreign Application Priority Data
Jun. 29, 2010 (DE) .................. 10 2010 017 630

(51) Int. Cl.
*G02B 21/36* (2006.01)
*G01N 21/64* (2006.01)
(Continued)

(52) U.S. Cl.
CPC ....... *G02B 21/365* (2013.01); *G01N 21/6428* (2013.01); *G01N 21/6458* (2013.01);
(Continued)

(58) Field of Classification Search
CPC .................................................. G02B 21/365
(Continued)

(56) References Cited

U.S. PATENT DOCUMENTS 7,227,981 B1    6/2007  Fleute et al.
7,675,045 B1    3/2010  Werner et al.
(Continued)

FOREIGN PATENT DOCUMENTS

DE    101 11 226 A1    9/2002
DE    600 09 113 T2    3/2005
(Continued)

OTHER PUBLICATIONS

Rust et al., "Sub-Diffraction-Limit Imaging by Stochastic Optical Reconstruction Microscopy (STORM)", Brief Communications, Nature Methods, Advance Online Publication, Aug. 9, 2006 (one (1) page).
(Continued)

*Primary Examiner* — Christopher S Kelley
*Assistant Examiner* — Jonathan Messmore
(74) *Attorney, Agent, or Firm* — Crowell & Moring LLP

(57) ABSTRACT

A method for light-microscopy imaging of a sample structure (2, 34) is described, having the following steps:
preparing the sample structure (2, 34) with markers that are transferrable into a state imageable by light microscopy,
generating a sequence of individual-image data sets by sequential imaging of the sample structure (2, 34), in such a way that for each image, only a subset of the totality of the markers is in each case transferred into the state imageable by light microscopy, the markers of the respective subset having an average spacing from one another which is greater than the resolution limit of light-microscopy imaging which determines the extent of a light distribution representing one of the respectively imaged markers,
generating at least two data blocks in which multiple successive individual-image data sets are respectively combined,
(Continued)

superposing the individual-image data sets contained in the respective data block to yield a superposed-image data set, identifying an image offset between the superposed-image data sets, correcting the individual-image data sets that are contained in at least one of the superposed-image data sets on the basis of the identified image offset, determining center point positions of the light distributions representing the imaged markers, and assembling the center point positions into an offset-corrected overall image.

14 Claims, 6 Drawing Sheets

(51) Int. Cl.
    *G02B 21/16*     (2006.01)
    *G02B 27/58*     (2006.01)

(52) U.S. Cl.
    CPC ........... *G02B 21/16* (2013.01); *G02B 21/367* (2013.01); *G02B 27/58* (2013.01)

(58) Field of Classification Search
    USPC ......................................................... 348/79
    See application file for complete search history.

(56) References Cited

U.S. PATENT DOCUMENTS

| | | | |
|---|---|---|---|
| 7,880,150 | B2 | 2/2011 | Hell et al. |
| 8,084,754 | B2 | 12/2011 | Hell et al. |
| 8,121,399 | B2 | 2/2012 | Hayashi et al. |
| 2005/0141081 | A1 | 6/2005 | Olschewski |
| 2006/0127084 | A1 | 6/2006 | Okada |
| 2008/0032414 | A1 | 2/2008 | Zhuang et al. |
| 2008/0182336 | A1* | 7/2008 | Zhuang et al. ............ 436/172 |
| 2008/0198694 | A1* | 8/2008 | Hansen .................... 367/96 |
| 2009/0134342 | A1 | 5/2009 | Hell et al. |
| 2009/0202155 | A1 | 8/2009 | Hayashi et al. |
| 2011/0182529 | A1 | 7/2011 | Kempe et al. |
| 2012/0018651 | A1 | 1/2012 | Hess et al. |

FOREIGN PATENT DOCUMENTS

| | | |
|---|---|---|
| DE | 10 2006 006 013 T2 | 10/2007 |
| DE | 10 2006 021 317 B3 | 10/2007 |
| DE | 11 2006 003 380 T5 | 10/2008 |
| DE | 11 2006 003 363 T5 | 1/2009 |
| DE | 10 2008 011 993 A1 | 9/2009 |
| DE | 10 2008 024 568 A1 | 12/2009 |
| DE | 10 2008 049 878 A1 | 4/2010 |
| EP | 1 548 485 A1 | 6/2005 |
| EP | 1 672 914 A2 | 6/2006 |
| JP | 2006-174069 A | 6/2006 |
| JP | 2008-73332 A | 4/2008 |
| JP | 2008-104886 A | 5/2008 |
| JP | 2008-259044 A | 10/2008 |
| JP | 2009-27724 A | 2/2009 |
| JP | 2009-300951 A | 12/2009 |
| JP | 2010-500563 A | 1/2010 |
| WO | WO 2006/127692 A2 | 11/2006 |
| WO | WO 2007/128434 A1 | 11/2007 |
| WO | WO 2008/091296 A2 | 7/2008 |
| WO | WO 2009/059378 A1 | 5/2009 |
| WO | WO 2010/062364 A1 | 6/2010 |

OTHER PUBLICATIONS

Geisler et al., "Resolution of λ/10 in Fluorescence Microscopy Using fast Single Molecule Photo-Switching", Applied physics A, Material Science & Processing, vol. 88, pp. 223-226, 2007.

German language Office Action dated Oct. 7, 2010 (six (6) pages).

International Search Report with English language translation dated Oct. 25, 2010 (seven (7) pages).

German language Written Opinion (PCT/ISA/237) dated Oct. 25, 2010 (seven (7) pages).

English language translation of International Preliminary Report on Patentability and Written Opinion (Five (5) pages).

* cited by examiner

METHOD AND DEVICE FOR LIGHT-MICROSCOPIC IMAGING OF A SAMPLE STRUCTURE

The invention relates to a method and a device for light-microscopy imaging of a sample structure.

In the recent past, light-microscopy imaging methods have been developed with which, based on a sequential, stochastic localization of individual markers (in particular, fluorescent molecules), it is possible to display sample structures that are smaller than the diffraction-related resolution limit of classic light microscopes. Such methods are described, for example, in WO 2006/127692 A2; DE 10 2006 021 317 B3; WO 2007/128434 A1, US 2009/0134342 A1; DE 10 2008 024 568 A1; "Sub-diffraction-limit imaging by stochastic optical reconstruction microscopy (STORM)," Nature Methods 3, 793-796 (2006), M. J. Rust, M. Bates, X. Zhuang; "Resolution of Lambda/10 in fluorescence microscopy using fast single molecule photo-switching," Geisler C. et al., Appl. Phys. A, 88, 223-226 (2007). This new branch of microscopy is also referred to as "localization microscopy." The methods applied are known in the literature, for example, under the designations PALM, FPALM, (F)STORM, PALMIRA, or GSDIM.

The new methods have in common the fact that the sample structures to be imaged are prepared with markers that possess two distinguishable states, namely a "bright" state and a "dark" state. For example, if fluorescent dyes are used as a marker, the bright state is then a fluorescence-capable state and the dark state is a non-fluorescence-capable state. In order for sample structures to be imaged at a resolution that is smaller than the classic resolution limit of the image-producing optic, a small subset of the markers is then repeatedly prepared into the bright state. This subset is referred to hereinafter as an "active subset." The active subset must be selected so that the average spacing between adjacent markers in the bright state—and thus the state capable of imaging by light microscopy—is greater than the resolution limit of the imaging optic. The luminance signals of the active subset are imaged onto a spatially resolving light detector, e.g. a CCD camera. A light distribution in the form of a spot of light, whose size is determined by the resolution limit of the image-producing optic, is therefore acquired from each marker.

The result is that a plurality of individual raw-data images are acquired in the form of individual-image data sets, in each of which a different active subset is imaged. In an image analysis process, the center points of the light distributions (representing the markers that are in the bright state) are then determined in each individual raw-data image. The center points of the light distributions identified from the individual raw-data images are then combined into one overall depiction in the form of an overall-image data set. The high-resolution overall image produced by this overall depiction reflects the distribution of the markers. "Raw data" are thus understood hereinafter as data that have not yet been subjected to the image analysis process in order to determine the center point positions.

For a representative reproduction of the sample structure to be imaged, a sufficiently large number of signals must be detected. But because the number of markers in the particular active subset is limited by the minimum average spacing that must exist between two markers in the bright state, a very large number of individual raw-data images must be acquired in order to image the sample structure completely. The number of individual raw-data images is typically in a range from 10,000 to 100,000.

The time required for acquiring an individual raw-data image is limited at the low end by the maximum image acquisition rate of the light detector. This leads to comparatively long total acquisition times for a sequence of individual raw-data images that is necessary for the overall depiction. The total acquisition time can thus amount to as much as several hours.

Motion of the sample being imaged, relative to the image-producing optic, can occur over this long total acquisition time. Because all the individual raw-data images must be combined after center-point determination in order to create a high-resolution overall image, any relative motion between the sample and the image-producing optic that occurs during the acquisition of two successive individual raw-data images degrades the spatial resolution of the overall image. In many cases this relative motion derives from a systematic mechanical motion of the system (also referred to as "mechanical drift") that is caused, for example, by thermal expansion or contraction, by mechanical stresses, or by a change in the consistency of lubricants that are used in the mechanical components.

The problems described above will be illustrated below with reference to FIGS. 1 to 3.

FIG. 1a schematically depicts a sample structure 2 that is made up of three concentric circular rings. It will be assumed in what follows that the structural features of this sample structure 2 that are to be imaged, in particular the spacings of the concentric circular rings from one another, are so small that they are below the diffraction-limited resolution limit of light-microscopy imaging.

When sample structure 2 shown in FIG. 1a is then provided with markers, and when these markers are brought into the bright state (in which they can thereby be imaged by light microscopy), what results because of the diffraction-limited resolution capability of light-microscopy imaging is a microscope image of the kind shown in FIG. 1b, in which the individual circular rings of sample structure 2 that are provided with markers are no longer distinguishable. In FIG. 1b (and also in FIGS. 2 and 3), sample structure 2 shown in FIG. 1a is indicated by dashed circular lines in order to illustrate the situation. As shown in FIG. 1b, the result here is a blurred and therefore spatially unresolved light distribution 4, indicated by hatching.

FIG. 2a shows a sequence of individual raw-data images, in each of which an active subset of markers is imaged. The active markers appear in the individual raw-data images as extended spots of light 6 whose size is determined by the resolution limit of the image-producing optic. As FIG. 2a shows, spots of light 6 are each at an average spacing from one another which is greater than this resolution limit that determines the size of spots of light 6.

FIG. 2b illustrates the manner in which center point positions 8 of spots of light 6 are identified, in the image analysis process mentioned above, from the individual raw-data images. Center point positions 8 determined from the individual raw-data images are then combined into an overall depiction shown in FIG. 2c. The overall depiction in 2c thus supplies a high-resolution overall image of sample structure 2 shown in FIG. 1a.

FIGS. 3a and 3b illustrate how a degradation of the spatial resolution of the overall image can occur as a consequence of a relative motion that takes place, during the acquisition of two successive individual raw-data images, between sample structure 2 being imaged and the image-producing optic. In this example, serving solely for illustration, the center point positions determined from a first individual raw-data image are assumed to be depicted by circles 10, and the center point positions determined from a second individual raw-data image immediately following it by squares 12.

FIG. 3*a* shows the ideal situation with no mechanical drift. Center point positions 10 and 12 identified from the two individual raw-data images precisely reproduce sample structure 2 shown in FIG. 1*a*. FIG. 3*b* depicts the case in which mechanical drift causes a displacement of the second individual raw-data image with respect to the first individual raw-data image. Center point positions 12 derived from the second individual raw-data image are correspondingly offset with respect to center point positions 10 derived from the first individual raw-data image. The result of this is a degradation in the spatial resolution of the overall image.

Some methods for compensating for mechanical drift are known. For example, it is proposed to mark the sample structure with reference markers, for example gold nanoparticles or fluorescent nanoparticles, and to sense their position optically, e.g. with a further detector, concurrently during image acquisition. Alternatively, mechanical drift can also be measured using suitable sensors, e.g. capacitive distance measuring devices. The sensed image offset can then be used to apply suitable control to a mechanism in order to compensate for drift, or to correct the identified center point positions. In every case, however, the outlay necessary for compensating for mechanical drift is comparatively high.

US 2008/0182336 A1 discloses a localization microscopy method in which provision is made for compensating for mechanical drift. For this, a correlation is calculated between individual images, and a correction variable is identified therefrom. Reference is further made to the documents U.S. Pat. No. 7,675,045 B1, DE 10 2008 049 878 A1, and WO 2010/062364 A1, in which further localization microscopy methods are disclosed.

The object of the invention is to describe a method and a device for light-microscopy imaging of a sample structure that enable reliable compensation for mechanical drift with little technical outlay.

The invention achieves this object, for the method, by means of the following steps:
  preparing a sample structure with markers that are transferrable into a state imageable by light microscopy,
  generating a sequence of individual-image data sets by sequential imaging of the sample structure, in such a way that for each image, only a subset of the totality of the markers is in each case transferred into the state imageable by light microscopy, the markers of the respective subset having an average spacing from one another which is greater than the resolution limit of light-microscopy imaging which determines the extent of a light distribution representing one of the respectively imaged markers,
  generating at least two data blocks in which multiple successive individual-image data sets are respectively combined,
  superposing the individual-image data sets contained in the respective data block to yield a superposed-image data set,
  identifying an image offset between the superposed-image data sets,
  correcting the individual-image data sets that are contained in at least one of the superposed-image data sets on the basis of the identified image offset,
  determining center point positions of the light distributions representing the imaged markers, and
  assembling the center point positions into an offset-corrected overall image.

The invention provides for combining the individual-image data sets into at least two (but as a rule more) data blocks, and superposing the individual-image data sets contained in the respective data block to yield a superposed-image data set. The superposed-image data sets then contain considerably more marker signals than each individual-image data set. The larger the respective data block, i.e. the more individual-image data sets are superposed to yield a respective superposed-image data set, the more complete the structural information that is contained in the respective superposed-image data set. The structural information contained in the superposed-image data sets is then used to identify an image offset between the respective successive superposed-image data sets.

The time resolution with which the respective image offset is identified correlates with the number of individual-image data sets that are contained in a respective superposed-image data set. The smaller that number, the higher the time resolution (assuming a constant image acquisition time for each individual image). It is therefore desirable to select the number of individual-image data sets that are combined into a respective superposed-image data set in such a way that on the one hand sufficient structural information is available to allow the image offset to be determined, and on the other hand the highest possible time resolution is achieved.

The method according to the present invention has the advantage that drift compensation can be attained without requiring separate measurement apparatuses for the purpose, or without additional preparation outlay, for example using reference markers. Drift can thus be compensated for in purely computational fashion using a suitable software program, in order to compensate for undesired mechanical motions of the sample structure relative to the image-producing system.

The method according to the present invention is usable in all known microscopy methods, in particular in all localization microscopy methods such as PALM, FPALM, (F)STORM, PALMIRA, or GSDIM. This is true regardless of how the processes of switching the markers (usually photoactivatable molecules) between the bright state (i.e. imageable by light microscopy) and the dark state are realized.

The number of successive individual-image data sets that are combined into the respective data blocks is preferably defined in such a way that a correlation coefficient that is created by cross-correlation between the data blocks is greater than a predetermined threshold value. Cross-correlation offers the capability of defining the block sizes in such a way that they are on the one hand as small as possible so that as many correction steps as possible can be performed, but on the other hand also sufficiently large that the data blocks contain enough structural information to determine a significant, real image offset that is not entirely stochastic in nature. The correlation coefficient here represents an indication of the significance of the structural information contained in the data blocks.

The number of successive individual-image data sets in a respective data block can also be determined in another way. For example, this number can be determined on the basis of the average spacing of the center point positions identified in a respective superposed-image data set. The number of markers sensed in a respective superposed-image data set can also be utilized to define the number of individual-image data sets that are superposed to yield the superposed-image data set. A further possibility is to analyze the stochastic distribution of the sensed markers in a respective superposed-image data set, and to determine therefrom the number of individual-image data sets.

This number need not be the same for the individual superposed-image data sets. Especially if the switching-off process, i.e. the conversion of the markers from the bright state into the dark state, is effected by bleaching (as is the case, for example, in WO 2006/127692 A3), it can be advantageous to allow the superposed-image data sets to become larger in chronological sequence.

In an advantageous embodiment of the method, an interpolation function is determined on the basis of the identified image offset, the values of said function constituting individual image offset values on the basis of which the individual-image data sets within the respective superposed-image data set are corrected. It is thereby possible to correct each individual-image data set contained in the respective superposed-image data set with a separate image offset value, thereby making possible even more precise drift compensation.

The center point positions of the light distributions representing the imaged markers can be determined before or after offset correction. In the former case, firstly the individual-image data sets that are contained in the at least one superposed-image data set are corrected on the basis of the identified image offset, and then the center point positions of the light distributions representing the imaged markers are determined. In the latter case, conversely, firstly the center point positions of the light distributions representing the imaged markers are determined in the individual-image data sets, and then the center point positions of the individual-image data sets that are contained in the at least one superposed data set are corrected on the basis of the identified image offset.

The image offset can be identified using a variety of methods. In a preferred embodiment, the image offset is identified in accordance with the "iterative closest point" (ICP) algorithm, as described for example in "Object Modeling by Registration of Multiple Range Images," Y. Chen and G. Medioni, Proc. IEEE Conf. on Robotics and Automation, 1991; and in "A Method for Registration of 3-D Shapes," P. Besl and M. McKay, Trans. PAMI, Vol. 14, No. 2, 1992. With this algorithm it is possible to adapt so-called point clouds to one another; coordinate transformations are determined for the point clouds in such a way that the spacings between the point clouds are minimized. This involves determining, for each point of the one point cloud, the respective closest point of the other point cloud. The sum of the squares of the spacings is minimized by adapting the transformation parameters. This is done iteratively until the optimum is found.

Identification of the image offset is not, however, limited to the methods recited above. For example, the image offset can also be identified by detecting a common substructure in the superposed-image data sets. Detection of the substructure occurs here by means of a suitable image analysis, e.g. edge detection or pattern recognition.

It is also possible to determine the image offset between two superposed-image data sets by cross-correlation.

In a further advantageous refinement of the method, a continuous time course of an image drift is identified, by repeatedly identifying the image offset in multiple cycles and by modifying from one cycle to the next the number of individual-image data sets combined into the data blocks. This means that the image offset analysis according to the present invention is repeated for different data block classifications, so as thereby to detect a continuous time course of the image drift.

It is preferable, in the context of identifying the image offset, to determine a quality parameter and to identify, on the basis of the quality parameter, a variable that indicates the resolution of the overall image. The methods recited above, e.g. the ICP algorithm or cross-correlation, allow the determination of characterizing parameters (e.g. variance matrices in the ICP algorithm, or cross-correlation coefficients) that represent an indication of, and thus a quality parameter for, the image superposition precision. Based on such quality parameters, the effective image resolution to be expected after successful drift compensation can then be indicated.

In a further advantageous refinement, the center point positions are determined in three spatial dimensions. This means that the drift compensation according to the present invention can occur not only in one plane (usually referred to as the X-Y plane), but additionally in a plane perpendicular to that plane (usually referred to as the Z direction). With regard to a so-called "three-D" application of this kind, reference is made for example to "Three-dimensional sub-100 nm resolution fluorescence microscopy of thick samples," Juette, Manuel F. et al., Nature Methods 5, 2008, pp. 527-529.

The method according to the present invention provides for correcting the individual-image data sets on the basis of the identified image offset. In addition to or instead of this method step, it is also possible to use the identified image offset to move a component of the light microscope in accordance with the identified image offset in order to compensate for a drift motion of the sample structure relative to an image-producing system of the light microscope. The aforementioned component of the light microscope is, for example, a sample holder on which the sample structure is held. Control can be applied to the microscope components, in this context, in a closed control loop. This refinement is associated with increased technical outlay, but is possibly advantageous in terms of compensating for mechanical drift along the optical axis, i.e. focal plane drift.

The invention further relates to a device having means for carrying out the method described above.

These means preferably encompass a graphics processor. A graphics processor (GPU) of this kind is particularly suitable for carrying out the method according to the present invention because of the good capability for parallelization of the method steps constituting the method. This applies in particular to the method steps of identifying the image offset and also of determining the center point positions of the light distributions representing the imaged markers.

The invention will be explained in further detail below with reference to the Figures, in which:

FIG. 1a schematically depicts an exemplifying sample structure whose structural features to be imaged by light microscopy are smaller than the resolution limit of light-microscopy imaging;

FIG. 4 shows, as an exemplifying embodiment, a light microscope 20 that is suitable for carrying out the method according to the present invention for imaging a sample structure.

Figure 1A:
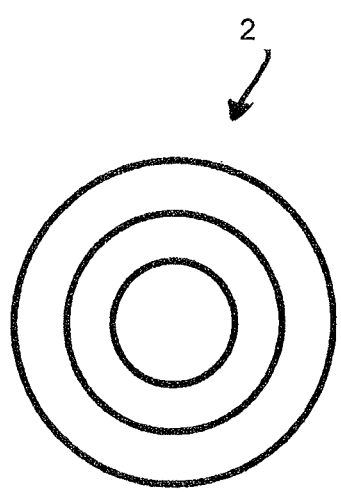
FIG. 1b is a schematic depiction showing a resolution-limited light-microscopy image of the sample structure according to FIG. 1a prepared with markers.
Figure 1B:
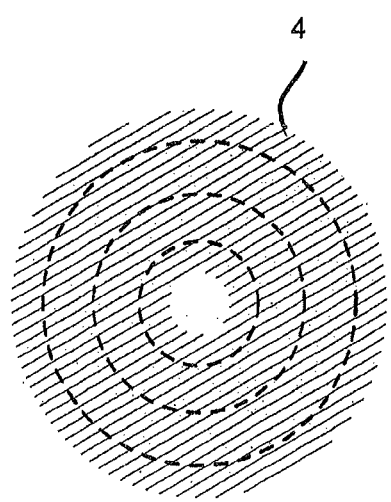
Figure 2A:
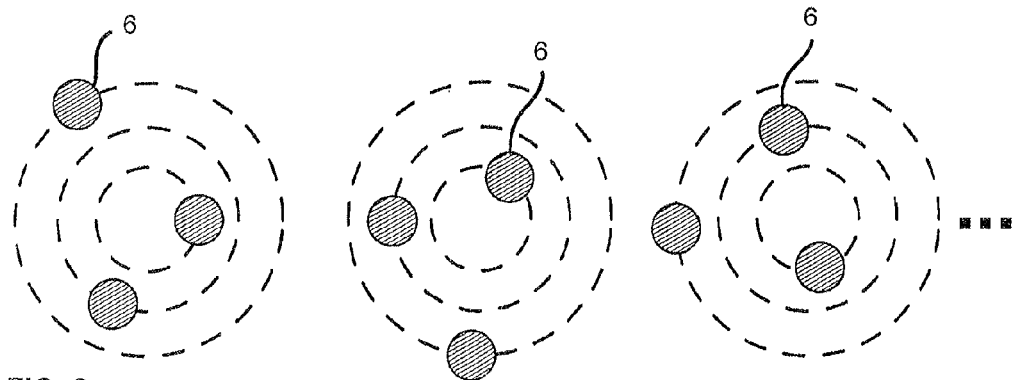
FIG. 2a shows a sequence of individual raw-data images in each of which an active subset of markers is imaged.
Figure 2B:
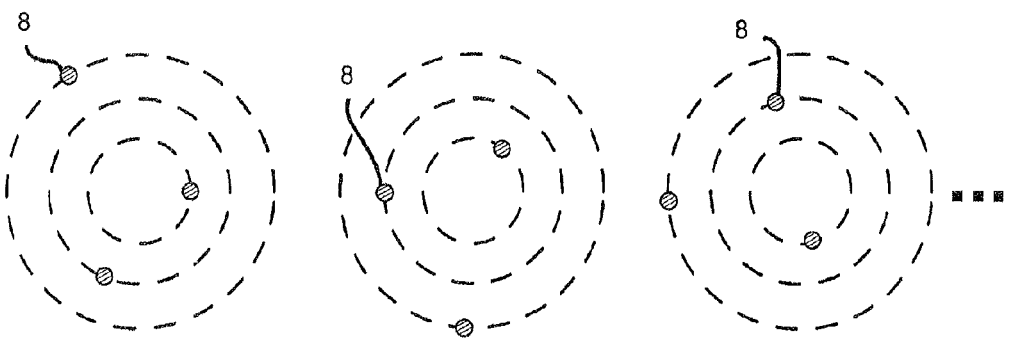
FIG. 2b shows a sequence corresponding to the image sequence of FIG. 2a, with center point positions identified from the individual raw-data images.
Figure 2C:
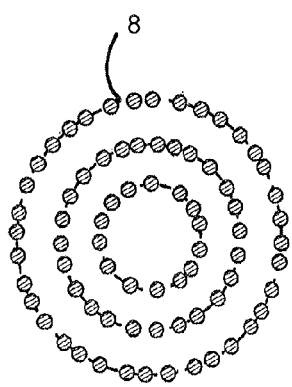
FIG. 2c is a high-resolution overall image in which the center point positions shown in FIG. 2b are combined.
Figures 3A, 3B:
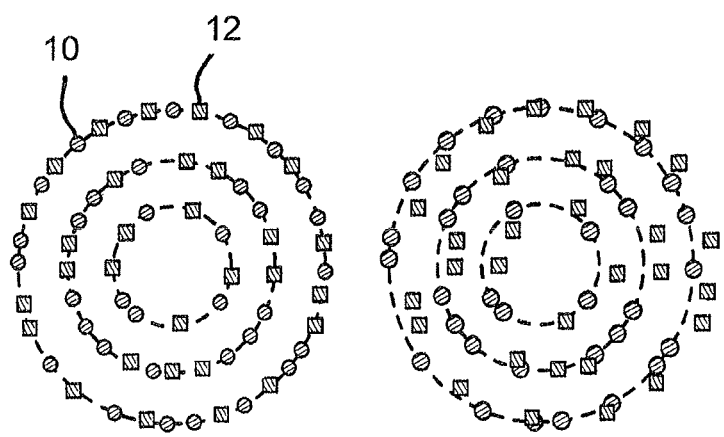
FIG. 3a is a drift-free overall image of the sample structure according to FIG. 1a, in which center point positions from two successive individual raw-data images are combined for illustrative purposes.
FIG. 3b is a drift-affected overall image of the sample structure according to FIG. 1a, in which, in accordance with FIG. 3a, center point positions of two successive individual raw-data images are combined.

Light microscope 20 encompasses a light source 22 that emits excitation light onto a lens system constituted from two lenses 24 and 26. This lens system serves to collimate in the desired manner the excitation light emitted from light source 22. The collimated excitation light is then incident onto a converging lens 28. Converging lens 28 focuses the excitation light into the aperture of an objective 30, the excitation light passing first through a dichroic mirror 32 that is transparent to the excitation light. The excitation light emerging from objective 30 is incident onto a sample structure 34 that is mounted on a specimen slide 36.

As explained previously, sample structure 34 is prepared with markers, e.g. fluorescent molecules. The methods recited previously can be utilized to transfer a respective portion of these markers into the bright state, and thereby generate an active subset.

The light emitted from sample structure 34 passes through objective 30 and is incident onto dichroic mirror 32. Dichroic mirror 32 is embodied so that it reflects the light emitted from sample structure 34, and thus directs it onto a lens 38 that concentrates the light onto a light detector 40, e.g. a CCD camera. Light detector 40 converts the received light into electrical signals, and outputs the latter to a graphics processor 42.

Figure 4:
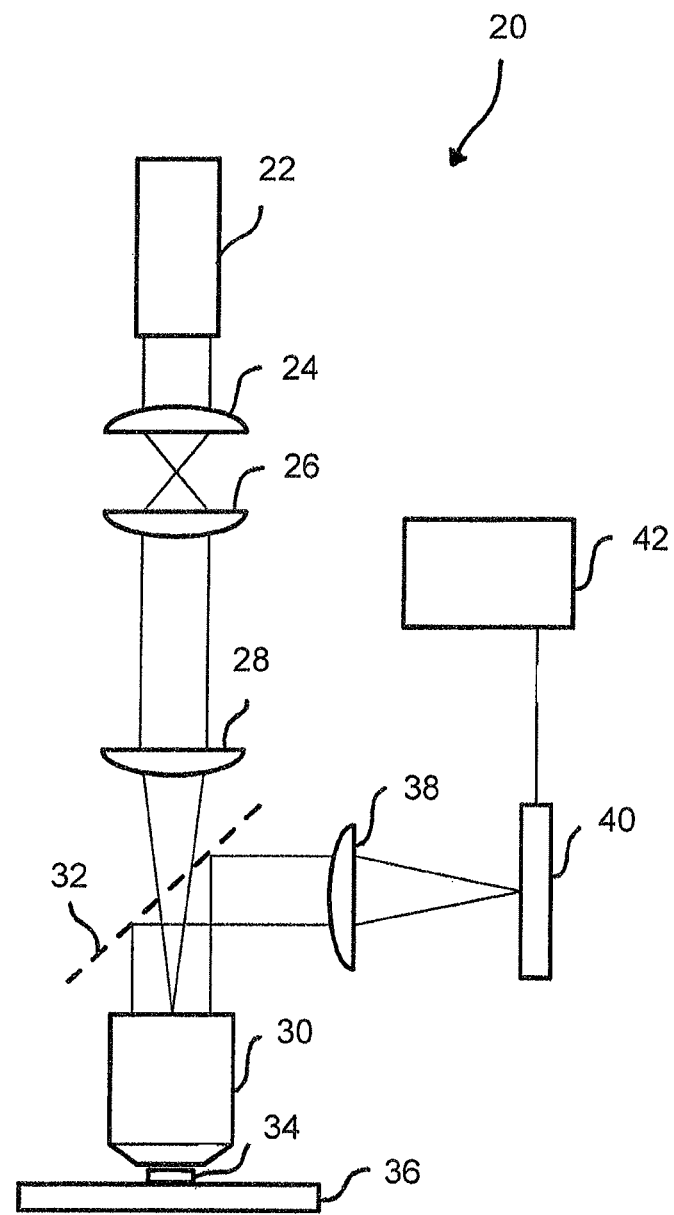
FIG. 4 shows the construction of a light microscope for carrying out the method according to the present invention.

An aspect according to the present invention of the method carried out by means of the light microscope of FIG. 4 will be illustrated below with reference to FIGS. 5a, 5b, and 5c. It is assumed here that sample structure 34, which is merely indicated in FIG. 4, is identical to sample structure 2 according to FIG. 1a.

Figure 5A:
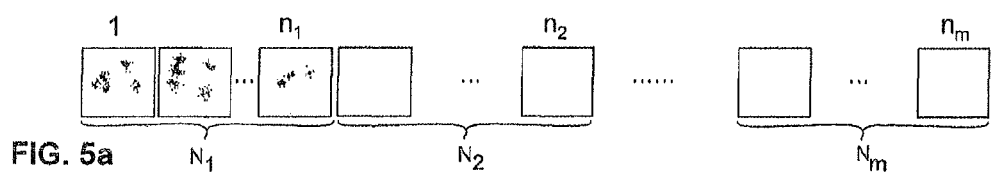
FIG. 5a shows a sequence of individual raw-data images that are combined into multiple data blocks.

FIG. 5a depicts a sequence of individual images serially numbered from 1 to $n_m$, where $n_m$ is a whole number greater than 1. Each of these individual images 1, . . . , $n_m$ depicts a different active subset of the markers with which sample structure 34 was prepared. The markers of a particular subset exhibit a spatial distribution in which they are at an average spacing from one another which is greater than the diffraction-limited resolution limit of light microscope 20 according to FIG. 4. For simplicity's sake, the light distributions that are generated by light-microscopy imaging of the markers are shown in FIG. 5a only for the first three of the individual images depicted.

The individual images 1, . . . , $n_m$ according to FIG. 5a generated by light detector 40 are converted into corresponding individual-image data sets that contain raw data processable by graphics processor 42. Once the individual-image data sets have been generated, they are combined into m data blocks as shown in FIG. 5a. In this example the first data block contains $N_1$ individual-image data sets, the second data block contains $N_2$ individual-image data sets, . . . and the m-th data block contains $N_m$ data sets.

The individual-image data sets contained in the respective data block are combined into a superposed-image data set. The $N_1$ individual-image data sets of the first data block thus yield a first superposed-image data set, the $N_2$ individual-image data sets of the second data block yield a second superposed-image data set, . . . and the $N_m$ individual-image data sets of the m-th data block yield an m-th superposed-image data set. The corresponding superposed images are shown in FIG. 5b. They contain (depending on the particular data block sizes $N_1, N_2, \ldots, N_m$) considerably more marker signals than each individual image.

The data block sizes $N_1, N_2, \ldots, N_m$ are selected so that on the one hand the superposed-image data sets contain sufficient structural information to allow identification of an image offset between two successive superposed-image data sets. On the other hand, the data block sizes $N_1, N_2, \ldots, N_m$ are also intended to be sufficiently small that as many data blocks as possible are created, and the image offset between each two successive superposed-image data sets can be identified as often as possible. The result is that image drift can be corrected with a high time resolution. An example of a method for determining suitable data block sizes $N_1, N_2, \ldots, N_m$ is described later on with reference to the flow chart of FIG. 6.

Figure 5B:
FIG. 5b shows superposed images in which the individual raw-data images combined into a respective data block are superposed.
Figure 5C:
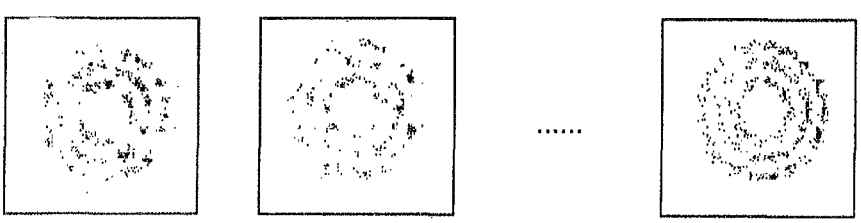
FIG. 5c shows superposed images which correspond to the images depicted in FIG. 5b and in which the identified center point positions are depicted.

The superposed-image data sets according to FIG. 5b contain the light distributions corresponding to the markers, the extent of said distributions being determined by the diffraction-limited resolution capability of light microscope 20. The superposed-image data sets therefore still contain the raw data, i.e. the data prior to center point correction. The image offset between the successive superposed-image data sets can be identified on the basis of the raw data themselves (i.e. based on the superposed-image data sets depicted in FIG. 5b), or after determination of the center point positions in the individual-image data sets and superposition of the center point positions. The data sets that are utilized in the latter case to identify the image offset are illustrated in FIG. 5c.

A concrete exemplifying embodiment for identification and correction, according to the present invention, of drift-related image offset is described below with reference to the flow chart of FIG. 6.

Firstly, in steps ST1 and ST2, suitable block sizes for the first and the second data block are determined. This means that the number of individual-image data sets contained in the respective data blocks is determined. In the present exemplifying embodiment, the cross-correlation method is used for this in step ST1: the cross-correlation (indicated by the ⊗ symbol) between the magnitude $S_1$ and the magnitude $S_2$ is calculated. The two magnitudes $S_1$ and $S_2$ constitute the superposed-image data sets recited above, $S_1$ being the sum or superposition of the individual-image data sets $A_n$ associated with the first data block, and $S_2$ being the sum or superposition of the individual-image data sets $A_m$ associated with the second data block. In step ST1 n and m each designate a control variable, and $n_1$ designates the number of the last individual-image data set of the first data block or of the first superposed-image data set, and $n_2$ designates the number of the last individual-image data set of the second data block or of the second superposed-image data set. At the beginning of the loop constituted by steps ST1 and ST2, $n_1$ is set to an initial value $\Delta$. The magnitude $C_1$ represents a cross-correlation matrix.

Once the cross-correlation matrix has been calculated for the first time in step ST1, step ST2 determines whether the maximum of matrix $C_1$, which is designated Max($C_1$) in step ST2, is greater than a predetermined threshold value SW The threshold value SW is predetermined in such a way that for the case in which Max($C_1$) is greater than the threshold value SW, the cross-correlation is significant, i.e. the two magnitudes S1 and S2 each contain structural information which is sufficient to determine an offset between the two corresponding superposed-image data sets. If Max($C_1$) in step ST2 is greater than the threshold value SW, the method continues with step ST3. Otherwise $n_1$ is incremented by $\Delta$, and step ST1 is executed again. The loop constituted by steps ST1 and ST2 is thus cycled through sufficiently often that Max($C_1$) is greater than the predetermined threshold value SW.

In step ST3, an average offset $\vec{d}_1$ between the first superposed-image data set corresponding to the first data block and the second superposed-image data set corresponding to the second data block is determined on the basis of the position of the magnitude Max($C_1$) within the cross-correlation matrix $C_1$, and saved. The method then proceeds with the loop constituted by steps ST4 and ST5. In step ST4, corresponding to step ST1, the cross-correlation between the two superposed-image data sets $S_i$ and $S_{i+1}$ is calculated in order to identify a cross-correlation matrix $C_i$. When step ST4 is executed for the first time, the control variable i is therefore equal to 2. This means that the cross-correlation between the second and the third superposed-image data set is being determined.

Step ST5 determines whether Max($C_1$) is greater than the threshold value SW. If so, i is incremented by 1 and the method jumps back to step ST4, in which the cross-correlation between the third superposed-image data set and the fourth superposed-image data set is then determined. If, on the other hand, the magnitude Max($C_1$) in step ST5 is not greater than the threshold value SW, $n_{i+1}$ is then incremented by $\Delta$, i.e. further individual-image data sets are added to the third superposed-image data set (in accordance with the magnitude of A). Steps ST4 and ST5 are then repeated sufficiently often that Max($C_1$) exceeds the threshold value SW.

Once the loop constituted by steps ST4 l and ST5 has been cycled through sufficiently often, and the control variable i has thus been increased to the point that the entire sequence of individual-image data sets (see FIG. 5a) has been divided into superposed-image data sets of suitable size, the average offsets $\vec{d}_1$ between the successive superposed-image data sets are determined and saved in step ST6.

Next, in step ST7, the individual-image data sets contained in the respective superposed-image data sets are corrected on the basis of a summed offset $$\sum_{i=1 \ldots i_{max}} \vec{d}_i,$$

where $i_{max}$ indicates the value of the control variable i after the last cycle through the loop constituted by steps ST4 and ST4 [sic]. This means that, for example, the individual-image data sets of the second superposed-image data set (i+1=2) are corrected with the average offset $\vec{d}_1$, the individual-image data sets of the third superposed-image data set (i+1=3) with the average offset ($\vec{d}_1+\vec{d}_2$), the individual-image data sets of the fourth superposed-image data set (i+1=4) with the average offset ($\vec{d}_1+\vec{d}_2+\vec{d}_3$), etc.

The center point positions of the light distributions, representing the imaged markers, in the individual-image data sets are then determined, and the center point positions thereby determined are assembled into an offset-corrected overall image in which image drift is compensated for.

Figure 6:
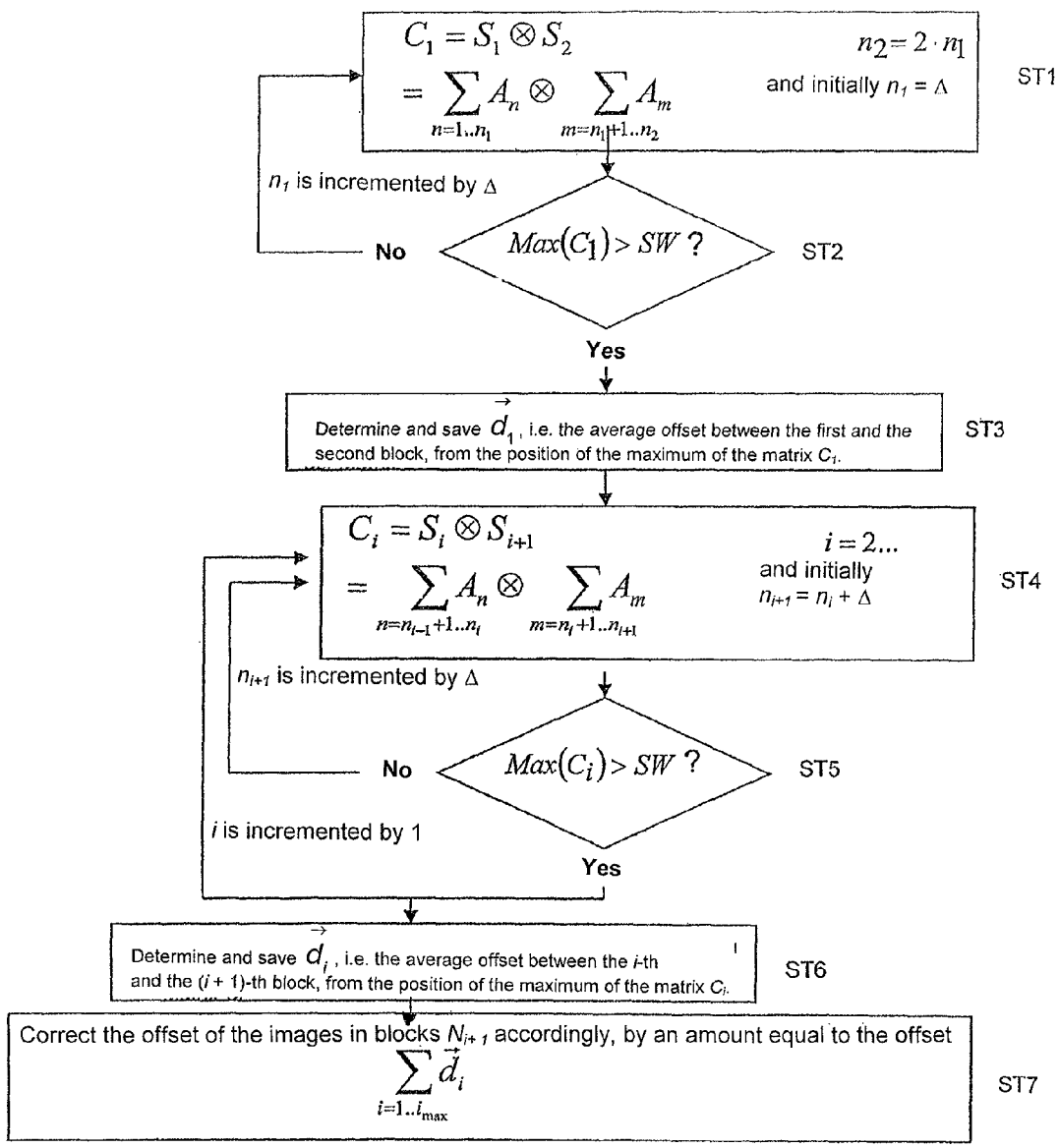
FIG. 6 is a flow chart with method steps according to the present invention for identifying and correcting a drift-related image offset.

The method depicted in FIG. 6 is to be understood as merely an example. In this exemplifying method, for example, identification of the image offset between the superposed-image data sets occurs on the basis of the raw data, i.e. on the basis of data that do not yet contain the center point positions of the light distributions that represent the imaged markers. It is likewise possible, however, first to identify the center point positions in the individual-image data sets, and only then to identify the image offset on the basis of the center point positions.

In the exemplifying embodiment described above, the image offset $\vec{d}_1$ is determined in each case between two immediately successive superposed-image data sets. It is likewise possible, however, to determine one of the superposed-image data sets (usefully the first superposed-image data set) as a reference data set, and then to identify the image offset of each of the subsequent superposed-image data sets relative to that reference data set.

The method depicted in FIG. 6 can also be modified in such a way that not just the image offset between the successive superposed-image data sets, but in addition the image offset between the individual-image data sets contained in the respective superposed-image data sets, is determined and then corrected. This can be done, for example, by identifying on the basis of the offsets $\vec{d}_1$ a function that, as it were, continuously interpolates the discrete magnitudes $\vec{d}_1$. By means of this interpolation function an image offset value can then be determined for each individual-image data set, and the respective individual-image data set can be correspondingly corrected. The result is that drift compensation becomes even more precise.

It should furthermore be noted that the identified image offset $\vec{d}_1$ can also be used to apply control directly to a component of light microscope 20, e.g. to sample holder 36, for drift compensation. For this, for example, graphics processor 42 can generate a control variable, corresponding to the image offset $\vec{d}_1$, with which a positioning member (not shown in FIG. 4), e.g. a motor, is controlled so as to move the aforementioned microscope component relative to objective 30 in such a way that a mechanical drift is compensated for. In this case it is possible in some circumstances to omit the above-described offset correction of the individual-image data sets.

The invention claimed is:

1. A method for localization light-microscopy imaging of a sample structure, wherein said light microscopy imaging has a resolution limit; said method comprising:
   preparing the sample structure with markers that are transferrable into a state imageable by light microscopy,
   generating a sequence of individual-image raw-data image sets by sequential imaging of the sample structure in such a way that for each image, only a subset of the totality of the markers is in each case transferred into the state imageable by light microscopy, the markers of the respective subset having an average spacing from one another which is greater than the resolution limit of light-microscopy imaging which determines the extent of a light distribution representing one of the respectively imaged markers, generating at least two data blocks in which multiple successive individual-image raw-data sets are respectively combined, superposing for each data block the individual-image raw-data sets contained in the respective data block to yield a corresponding superposed-image data set, identifying a drift-based image offset between the superposed-image data sets of the at least two data blocks, wherein identification of the drift-based image offset is based on the imaged sample structure itself, correcting the individual-image data sets that are contained in at least one of the superposed-image data sets of one of the data blocks on the basis of the identified image offset, determining center point positions of the corrected individual-image data sets of the light distributions representing the imaged markers, and assembling the center point positions into an offset-corrected overall localization microscopy image, wherein the step of determining center point positions is performed after the step of correcting the individual-image data sets, wherein the individual-image raw-data sets contained in the at least one superposed-image data set first are corrected based on the identified image offset, and the center point positions of the light distributions representing the imaged markers then are determined.

2. The method according to claim 1, wherein the number of successive individual-image data sets that are combined into the respective data blocks is defined in such a way that a correlation coefficient that is created by cross-correlation between the data blocks is greater than a predetermined threshold value.

3. The method according to claim 1, wherein
more than two image data sets are superposed, and one of the superposed-image data sets is determined as a reference data set, and
the image offset of each of the other superposed-image data sets is determined relative to the reference data set.

4. The method according to claim 1, wherein more than two image data sets are superposed, and the image offset is determined in each case between two immediately successive superposed-image data sets.

5. The method according to claim 1, wherein
an interpolation function is determined based on the identified image offset;
said interpolation function defining values constituting individual image offset values, and
the individual-image data sets within the respective superposed-image data set are corrected based on said individual image offset values.

6. The method according to claim 1, wherein
the center point positions of the light distributions representing the imaged markers first are determined in the individual-image data sets, and
the center point positions of the individual-image data sets contained in the at least one superposed-image data set then are corrected based on the identified image offset.

7. The method according to claim 1, wherein the image offset is identified in accordance with an ICP algorithm.

8. The method according to claim 1, wherein the image offset is identified by detecting a common substructure in the superposed-image data sets.

9. The method according to claim 1, wherein a continuous time course of an image drift is identified by repeatedly identifying the image offset in multiple cycles and by modifying from one cycle to the next the number of individual-image data sets combined into the data blocks.

10. The method according to claim 1, wherein
a quality parameter is determined during the identification of the image offset, and
a variable that indicates the resolution of the overall image is identified based on said quality parameter.

11. The method according to claim 1, wherein the center point positions are determined in three spatial dimensions.

12. The method according to claim 1, further comprising moving a component of a light microscope in accordance with the identified image offset in order to compensate for a drift motion of the sample structure relative to an image-producing system of the light microscope.

13. A light microscope comprising means for carrying out the method according to claim 1.

14. The microscope according to claim 13, wherein said means include a graphics processor.

* * * * *